United States Patent [19]

Lemaire et al.

[11] Patent Number: 5,082,955
[45] Date of Patent: Jan. 21, 1992

[54] METHOD OF SEPARATING ISOMERS OF A CROWN ETHER COMPOUND TO RECOVER CIS-SYN-CIS ISOMER FROM DICYCLOHEXYL 18-CROWN 6.

[75] Inventors: Marc Lemaire, Villeurbanne; Alain Guy, Pontcarre; Jacques Foos, Orsay; Vincent Guyon, Paris; Rodolphe Chomel, Orange, all of France

[73] Assignee: Cogema-Compagnie Generale Des Matieres Nuclearires, Villacoublay, France

[21] Appl. No.: 625,552

[22] Filed: Dec. 11, 1990

[30] Foreign Application Priority Data

Dec. 15, 1989 [FR] France ................... 89 16637

[51] Int. Cl.$^5$ ........................... C07D 323/00
[52] U.S. Cl. ....................... 549/349; 549/352; 549/353; 423/11; 534/11
[58] Field of Search .............. 549/352, 353, 349; 423/11; 534/11

[56] References Cited

U.S. PATENT DOCUMENTS 3,687,972 8/1972 Dedersen .................. 549/349

FOREIGN PATENT DOCUMENTS 1014237 7/1984 U.S.S.R. .................. 549/349
1268583 11/1986 U.S.S.R. .................. 549/349

OTHER PUBLICATIONS

Chemical Abstracts, vol. 110, No. 7, 13/2/89, P. J. Zheng et al.
Chemical Abstracts, vol. 102, No. 1, 7/1/1985, N. A. Tsarenko et al.
Chemical Abstracts, vol. 108, No. 3, 18/1/1988, V. V. Yaksin et al.
Inorganic Chemistry, vol. 14, No. 12, Dec. 1975, R. M. Izatt et al.
Wang et al., Extraction Equilibrium of Uranium (VI) with Dicyclohexano-18-Crown 6 . . . , J. Radioanal Nucl. Chem., vol. 98 (1) 11-16.
Parsons, Synthesis of Ten Isomers of a Macrocyclic Polyether Tetramethyl-dibenzo-18-Crown-6, and their Complexes with Salts of Alkali Metals.
J. Chem. Soc. Perkin Trans. I(GB), No. 3, pp. 245-250.

Primary Examiner—Brooks H. Hunt
Assistant Examiner—Ngoclan T. Mai
Attorney, Agent, or Firm—Pearne, Gordon, McCoy & Granger

[57] ABSTRACT

A method for separating the isomers of a crown ether compound and making it possible to recover in particular the pure cis-syn-cis isomer from DCH 18C6 includes:

a) dissolving in an organic solvent a mixture of the isomers of said crown compound including the cis-anti-cis isomer and the cis-syn-cis isomer, b) adding uranyl nitrate to the solution obtained in stage a) in sufficient quantities so that virtually all of the isomers, except the cis-syn-cis isomer, are precipitated in the form of complexes with the uranyl nitrate, c) separating the formed precipitate, d) recovering the cis-syn-cis isomer from the solution, and e) recovering the cis-anti-cis isomer from the precipitate.

9 Claims, 2 Drawing Sheets

METHOD OF SEPARATING ISOMERS OF A CROWN ETHER COMPOUND TO RECOVER CIS-SYN-CIS ISOMER FROM DICYCLOHEXYL 18-CROWN 6.

FIELD OF THE INVENTION

The object of the present invention is to provide a method to separate the isomers of crown compounds and making it possible to in particular isolate the cis-syn-cis isomer from DCH 18C6.

BACKGROUND OF THE INVENTION

More specifically, it concerns the separation of the isomers of crown compounds with the formula:

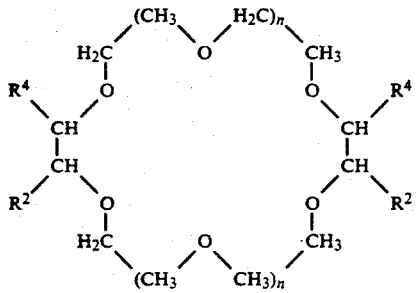

in which n=0 or is a whole number ranging from 1 to 3, $R_1$ and $R_2$, which are identical or different, are alkyl or alkoxyalkyl radicals or $R_1$ and $R_2$ collectively form a cycloalkyl radical.

From these crown compounds, dicyclohexyl 18-Crown-6 (DCH18C6) which responds to the formula:

(II)

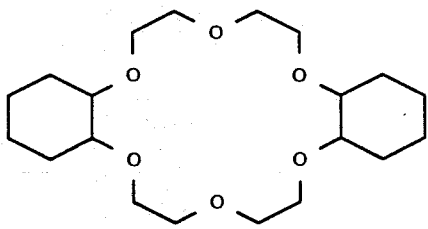

is a substance commercially available in the form of a mixture of several isomers.

In fact, this product has 5 diastereoisomers having the following structures:

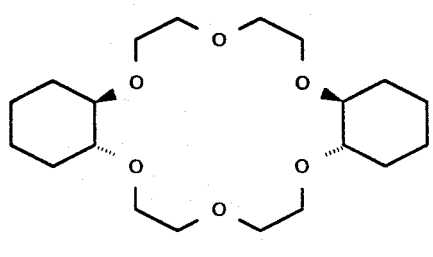

trans-syn-trans

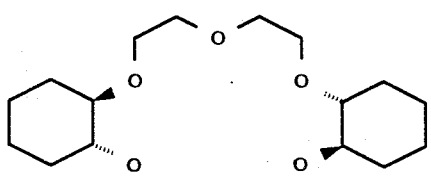

trans-anti-trans

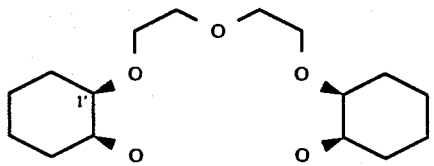

cis-syn-cis A

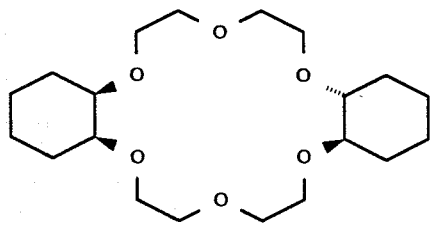

cis-trans

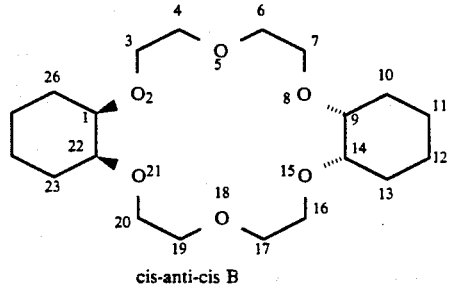

cis-anti-cis B crystalline form B1: 69-70° C.
crystalline form B2: 83-84° C.

When the DCH18C6 is obtained via the catalytic hydrogenation of dibenzo-18-Crown-6, as is the case with commercial products, it mainly contains cis-syn-cis (isomer A) and cis-anti-cis (isomer B) isomers.

For certain applications, it may be advantageous to use one of the pure isomers rather than the mixture of isomers. However, all the known methods to date to separate these various isomers with satisfactory yields are difficult to implement on an industrial scale.

One of these known methods is a method to separate the isomers from DCH18C6 via chromatography on an aluminium column, this method using a hexane/ether mixture whose ether concentration gradient gradually increases so as to elute the isomer A, and methanol to collect the isomer B. This method described by R. M. Izatt and al in J. Amer. Chem. Soc., 93, 1619 (1971) has the drawback of being long and expensive to implement and only provides yields of 20 to 30% for each of the isomers.

R. N. Izatt and al have described in Inorganic Chemistry, 14, 3132 (1975) another method to separate the isomers from DCH18C6 by a method based on the selective precipitation of the lead DCH18C6/perchlorate complex of the isomer B (cis-anti-cis).

After separation of the precipitate including the isomer B by filtering and processing the filtrate with $H_2S$ to eliminate the lead, the isomer A (cis-syn-cis) remaining in the solution is recovered by adding perchloric acid so as to precipitate the isomer A. Although this method results in obtaining high yields, it may not be used easily on an industrial scale, as it requires the use of the heavy metal perchlorates known to be explosive and sulphurated hydrogen known to be toxic.

Another method for separating isomers from DCH18C6 described by C. J. Pedersen in Organic Syntheses, 52, 66, uses crystallization of the potassium acetate/DCH18C6 complex in a petroleum ether/$CH_2Cl_2$ mixture.

This method has the drawback of only being suitable for separation of the isomer B (cis-anti-cis) and only results in obtaining a yield of 12%.

Therefore, the known methods for separating the isomers from DCH18C6 are either less high-performing, expensive and long, or are impossible to implement on an industrial scale.

SUMMARY OF THE INVENTION

The object of the present invention is to provide a method to separate isomers from a crown compound, such as DCH18C6, which mitigates these drawbacks.

According to the invention, the method for separating the isomers from a crown compound with the formula:

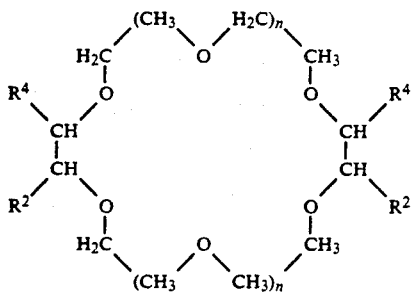

in which n=0 or is a whole number ranging from 1 to 3, $R_1$ and $R_2$, which are identical or different, represent an alkyl radical, an alkoxyalkyl radical or a poly(alkoxyalkyl) radical or $R_1$ and $R_2$ collectively form a cycloalkyl radical, wherein it includes the following successive stages:

a) dissolving in an organic solvent a mixture of the isomers of said crown compound including the cis-anti-cis isomer and the cis-syn-cis isomer, b) adding uranyl nitrate to the solution obtained in stage a) in sufficient quantities so that virtually all the isomers, except the cis-syn-cis isomer, of the crown compound are precipitated in the form of complexes together with the uranyl nitrate, c) separating the formed precipitate, and d) recovering the remaining pure cis-syn-cis isomer from the solution.

In the formula (I) given above, $R_1$ and $R_2$ may be identical or different and represent alkyl, alkoxyalkyl or poly(alkoxyalkyl) radicals.

The alkyl and alkoxyalkyl radicals may be linear or branched and comprise between 1 and 10 carbon atoms. By way of example of such radicals, these may be methyl, ethyl, propyl, isopropyl, butyl, tert-butyl, isobutyl, methoxymethyl, ethoxymethyl, methoxyethyl or methoxybutyl radicals.

Poly(alkoxyalkyl) radicals are alkyl radicals comprising several ether-oxide functions. They may satisfy the formula:

in which R is a bivalent alcoylene radical, for example methylene, and X is a polyoxyalkylene radical derived from polyethyleneglycols, for example a radical with the formula:

in which n, m, p, r and s are whole numbers ranging from 1 to 4 and $R_4$ is an alkyl radical.

When $R_1$ and $R_2$ collectively form a cycloalkyl radical, it preferably has between 3 and 6 carbon atoms.

The mode for separation used in the method of the invention is based on the solubility difference in the organic solvent used of the cis-syn-cis isomer and the complex formed between the cis-anti-cis isomer and uranyl nitrate.

It is also based on the use of a suitable quantity of uranyl nitrate so as to ensure that all the isomers of the crown compound, except for the cis-syn-cis isomer, are precipitated in the form of complexes, whereas the cis-syn-cis isomer remains in the solution.

The quantity of uranyl nitrate to be used depends in particular on the nature of the crown compound, the precipitation conditions and the isomer B content of the mixture. In the case of DCH18C6, good results are obtained when 3.5 mols of uranyl nitrate is used per mol of the isomer B.

The optimal quantity may be determined easily by routine tests, as shall be seen subsequently.

In this method, the quantity of the uranyl nitrate to be used depends on the isomer B (cis-anti-cis) content of the initial mixture.

Also, it is necessary to firstly determine the content of the isomer B. This may be evaluated, for example, by analyzing the mixture by means of nuclear magnetic resonance.

Generally speaking, the commercial mixtures of isomers of crown compounds, such as DCH18C6, contain from 46 to 65% of cis-syn-cis isomers and from 37 to 40% of cis-anti-cis isomers.

According to one preferred mode for implementing the method of the invention, first of all a stage is carried out consisting of separating one portion of the isomer B (cis-anti-cis) present in the initial isomer mixture so as to process a mixture enriched with the sought-after isomer, namely the isomer A, and of accordingly using a smaller quantity of uranyl nitrate.

This preliminary stage may be effected by dissolving the mixture in an organic solvent, crystallizing the isomer B present in this solution and separating the crystallized isomer B.

In fact, it has been observed that when a mixture of crown compound isomers is dissolved in a suitable solvent and when recrystallization is next carried out at ambient temperature, the crystallized substance is constituted by the pure isomer B in the crystalline form B1 in the case of DCH18C6 or is enriched with the isomer B. Accordingly, the solution is enriched with the isomer A with respect to the initial mixture.

The organic solvents which make it possible to obtain such an enriching may be saturated aliphatic hydrocarbons or aromatic hydrocarbons.

By way of example of saturated aliphatic hydrocarbons, these may be pentane, heptane and isooctane. In the case of DCH18C6, the heptane and pentane result in crystallization of the pure isomer B, whereas the isooctane results in obtaining a crystallized substance containing 14.7% of the isomer A; it is preferable to use heptane which is more efficient than pentane for enriching the solution with the isomer A.

The organic solvents used for the stage for precipitating complexes with uranyl nitrate are of the same type since the separation principle of these complexes is also based on a solubility difference of the complexes in the solvent.

Also, in the case where the crown compound is DCH18C6, it is preferable to also use heptane for the precipitation stage b).

According to the method of the invention, it is possible to recover the isomer B (cis-anti-cis) from the precipitate separated in stage c).

With this aim in mind, it is possible to decompose the complex via a treatment with water and chloroform so as to free the pure isomer B and recover the uranyl nitrate which thus may be reused.

The isomer A which remains in the solution may be recovered in its pure state by evaporating the solvent.

Thus, the method of the invention is easy to implement. Furthermore, the reacting agents used do not pose any problem with regard to safety or provisioning. In fact, the main reactive agent is depleted uranyl nitrate which is a by-product from plants for the isotopic enriching of uranium.

BRIEF DESCRIPTION OF THE DRAWINGS

Other characteristics and advantages of the invention shall appear more readily from a reading of the following examples, given by way of illustration and being in no way restrictive, with reference to the accompanying drawing on which.

DETAILED DESCRIPTION OF THE PREFERRED EMBODIMENTS

Figure 1:
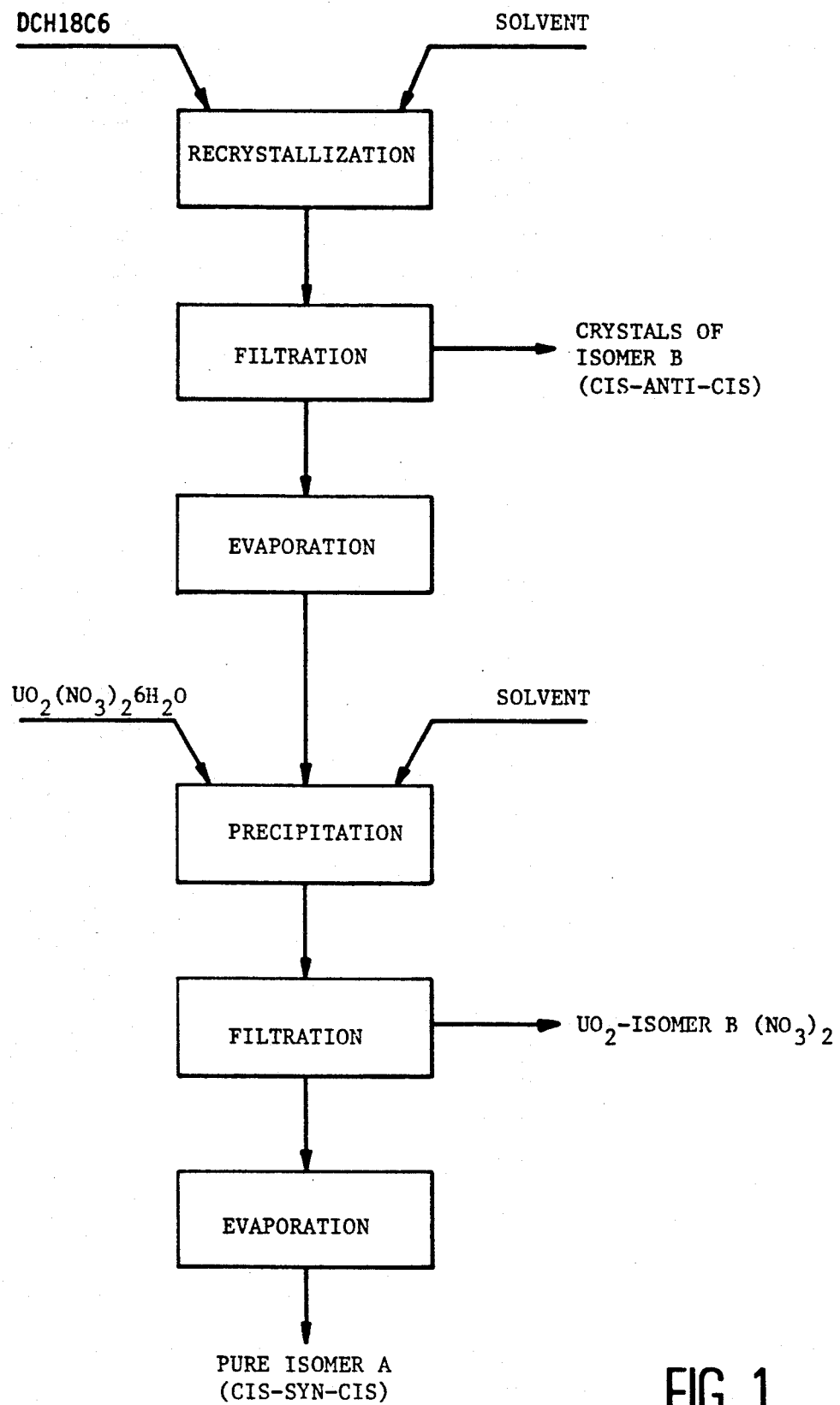
FIG. 1 is a diagram illustrating a mode for implementing the method of the invention.

FIG. 1 diagrammatically shows a mode for implementation of the method of the invention and comprising the preliminary stage for recrystallization of the cis-anti-cis isomer.

As shown on FIG. 1, first of all the stage for recrystallization of the isomer B (cis-anti-cis) is carried out.

With this aim in mind, the commercial mixture of the isomers of DCH18C6 is dissolved in a suitable solvent, such as heptane, then the isomer B is recrystallized from this solution at ambient temperature.

After this recrystallization, the crystals of the isomer B are separated by filtering the solution and then the solution is evaporated so as to collect a mixture of the isomers of DCH18C6 enriched with the isomer A (cis-syn-cis).

So as to carry out the next stage for precipitation by uranyl nitrate, first of all the mixture is analyzed by nuclear magnetic resonance of the 13C so as to determine the content of the isomer B.

Figure 2:
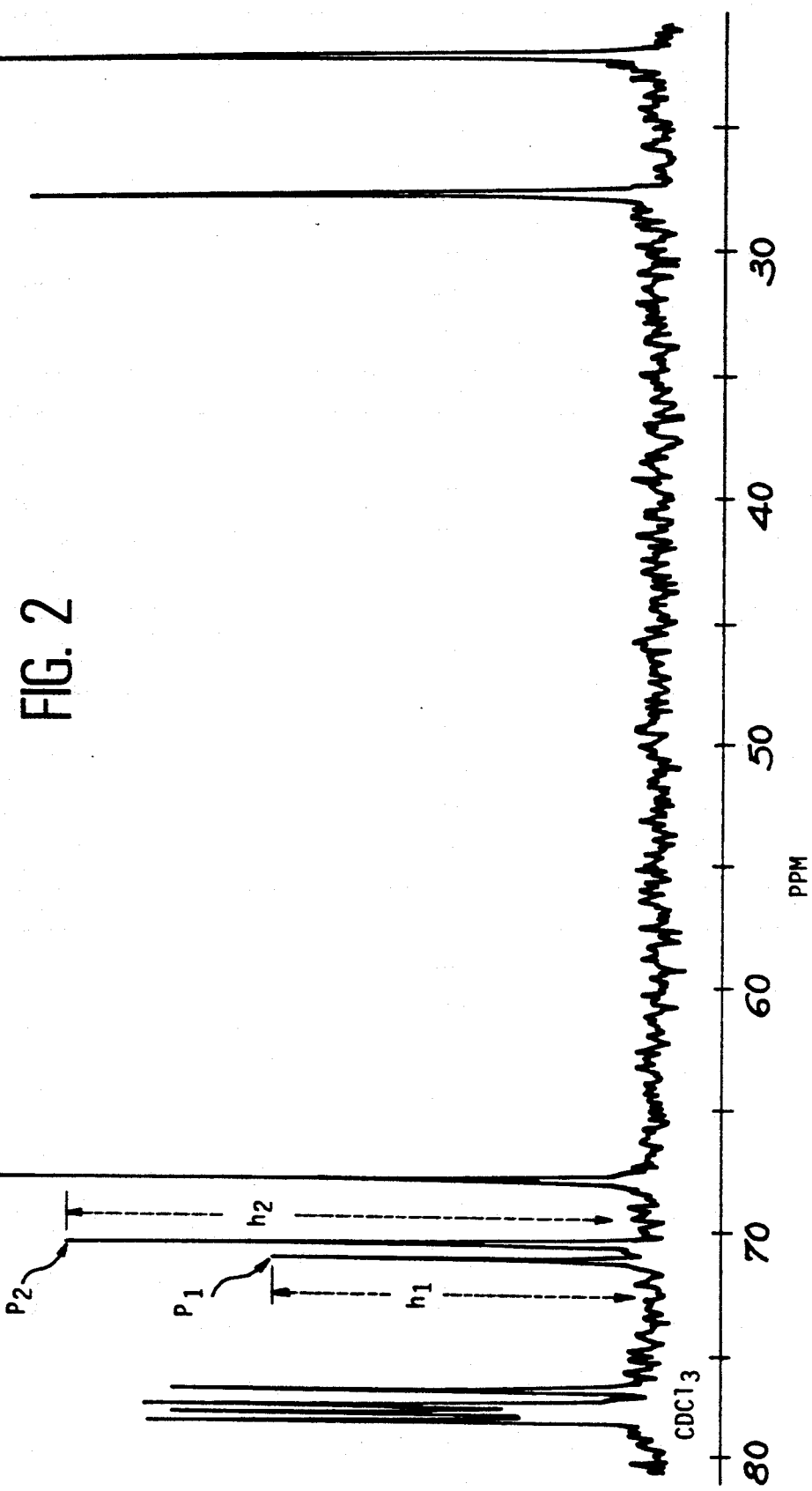
FIG. 2 is an RMN 13C spectrum of a commercial mixture of DCH18C6 isomers.

Thus, a spectrum, such as the one shown on FIG. 2, is obtained. In this spectrum, the peak $P_1$ corresponds to the isomer A, whereas the peak $P_2$ corresponds to the isomer B. Thus, it is possible to assess the percentage of the isomer B in the mixture via the following formula:

$$\% B = \frac{h_2}{h_1 + h_2}$$

in which $h_1$ represents the height of the peak $P_1$ and $h_2$ represents the height of the peak $P_2$.

Following this assessment, a quantity of a suitable solvent and the desired quantity of uranyl nitrate is added to the isomer mixture, this uranyl nitrate corresponding to about 3.5 mols of uranyl nitrate per mole of the isomer B in the case of DCH18C6 so as to precipitate the uranyl nitrate/isomer B complex.

The amount of solvent used depends on the nature of the solvent. In the case of heptane, it is possible to use about 40 ml of solvent per gram of the isomer mixture.

It is possible to carry out the precipitation reaction at ambient temperature, preferably agitated, and this process lasts for a sufficient period, such as 24 hrs, so as to precipitate all the uranyl nitrate/isomer (apart from the isomer A) complexes.

When precipitation has been completed, the solution is filtered so as to firstly collect a solution of the pure isomer A from the solvent, and secondly collect a precipitate including the isomer B/uranyl nitrate complex.

So as to obtain the pure isomer A, the solution is evaporated.

So as to recover the isomer B, the complex is decomposed by processing with water and chloroform, which makes it possible to also recover the uranyl nitrate.

The following examples illustrate the separation of the isomers from DCH18C6 (examples 1 to 9) and from DCH24 and the use of the cis-syn-cis isomer of DCH18C6 so as to extract the plutonium (example 11).

EXAMPLE 1

24.6 g of DCH18C6 containing 62.9% of the isomer A (15.47 g), 37% of the isomer B (9.1 g) and less than 1% of the other isomers are dissolved in 74 ml of heptane and the isomer B is recrystallized from this solution for 24 hrs at ambient temperature. Thus, 3.4 g of the crystallized isomer B is collected by filtering.

Then the solution is evaporated and 21.2 g of an isomer mixture is collected, now having an isomer A content of about 73%.

Then 850 ml of heptane and 108 ml of a 25% weight solution of uranyl nitrate $(NO_3)_2 UO_2 \cdot 6H_2O$ are added to this mixture, all the above being agitated for 24 hrs at ambient temperature. Then the precipitate formed is filtered and dried in an oven at 60° C. for 20 hrs. Thus, 12 g of the precipitate is obtained and is dissolved in 300 ml of chloroform and 150 ml of distilled water. Next, the organic phase is dried on $MgSO_4$, the solvent is filtered and evaporated under vacuum, which yields 5.6 g of the isomer B, namely a yield of 98.9%, and the isomer A is recovered from the filtration solution by evaporating the solvent. Thus, 15.4 g of the isomer A is obtained, namely a yield of 99.5%.

This method thus makes it possible to quantitatively recover the isomers A and B with a yield of more than 99% for the isomer A.

Moreover, this method only uses less expensive products and it is also possible to quantitatively recover the used uranyl nitrate.

EXAMPLES 2 TO 8

In these examples, the same mode of operation is used as in example 1 so as to embody the precipitation of an isomer B/uranyl nitrate complex from 500 mg of an isomer mixture of DCH18C6 containing 68.8% of the isomer A (344 mg) by using 20 ml of heptane and different quantities of the uranyl nitrate solution so as to have different isomer B/uranyl nitrate molar ratios and a period of precipitation of 3 hrs in examples 2 to 7 and 24 hrs in example 8.

In each case, the percentage of the isomer A obtained is determined in the separated solution after the solvent has been evaporated.

The results and conditions of these examples are given in the annexed table.

In view of the results of this table, only the example 8 results in a 100% purity in the isomer A of the collected solution after filtering of the precipitate. This corresponds to an isomer B/uranyl nitrate molar ratio of 3.6 and to an agitation period of 24 hours.

Thus, the method of the invention is extremely advantageous since it makes it possible to quantitatively separate the isomers from DCH18C6 and to recover the isomer A with a 100% degree of purity.

EXAMPLE 9

In this example, some DCH18C6 containing 54% of the isomer A and 46% of the isomer B is dissolved in 3 volumes of heptane and the isomer B is recrystallized from this solution at $-5°$ C. Thus, one quantity of the isomer B representing 11.8% of the initial mixture is collected by filtering.

The solution is evaporated and a mixture of isomers is collected having an isomer A content of 66% and an isomer content of 34%.

Then 8 volumes of heptane and 2 volumes of $UO_2^{2+}$ is added to the mixture over a period of 2 hours and is agitated for 48 hours.

The precipitate is collected by filtering and is dissolved in water and chloroform. The organic solution obtained is distilled, which gives the isomer B with a B titer of 97%.

The isomer A is recovered from the filtration solution by evaporation with an A titer of 90%.

EXAMPLE 10

In this example, 1 g of an isomer mixture of DCH18C6, namely of the crown compound of formula (I) with n=2 containing 47% of the cis-anti-cis isomer and 53% of the cis-syn-cis isomer, is dissolved in 3 ml of heptane and 1.5 ml of uranyl nitrate $UO_2(NO_3)_2.6H_2O$ is added to this under agitation.

The precipitate formed is separated by filtering and is dissolved in a mixture of water and chloroform. Then the organic phase is dried on $MgSO_4$ and the solvent is evaporated under vacuum, the cis-anti-cis isomer then being recovered.

Then the cis-syn-cis isomer is recovered from the separated heptane solution.

The isomer A of the DCH18C6 may be used advantageously instead of the isomer mixture (A and B), especially for the extraction of plutonium in methods for reprocessing irradiated nuclear fuels, as shown in the example appearing below.

EXAMPLE 11

In this example, a nitric acid solution containing:
906 mg/l of uranium (VI)
136 mg/l of plutonium (IV)
$18.1 \times 10^1$ Bq/l (4.88 mCi/l) of fission products, and
5 mols/l of HNO
is processed by an organic solvent constituted by chloroform containing 0.134 mols/l of the cis-syn-cis isomer of the DCH18C6 obtained in example 1.

With this aim in mind, 15 ml of the aqueous solution is placed in contact with 30 ml of the organic extraction solvent under agitation for 10 mins. Then the two phases are separated by decantation and a measurement is made of their respective contents of uranium, plutonium and fission products and the splitting coefficients Dm of the uranium, the plutonium and the fission products are calculated between the two phases. This splitting coefficient Dm corresponds to the ratio of the concentration of the element in the organic solvent to the concentration of the same element in the aqueous solution.

The results obtained are given in table 2 appearing hereafter.

This table also indicates the values of the extraction constants Kex of the plutonium and the uranium which have been calculated from the values obtained.

In the light of this table, it appears that the plutonium splitting and extraction coefficients are much greater than those of uranium.

By way of comparison, the table also gives the results obtained by processing the same aqueous solution with two organic solvents respectively constituted by the chloroform containing 0.134 mols/l of the cis-anti-cis isomer of DCH18C6 and by the chloroform containing 0.134 mols/l of the isomer mixture of commercial DCH18C6.

In the light of this table 2, it appears that the cis-syn-cis isomer makes it possible to attain results much better than those obtained with the cis-anti-cis isomer and the isomer mixture.

TABLE I

| TEST | HEPTANE (ml) | DCH18C6 AT 68.8% (mg) | SOLUTION OF $(NO_3)_2UO_2$, $6H_2O$ at 25% (ml) | MOLE OF $UO_2^{2+}$ MOLE OF B | AGITATION PERIOD (h) | A % IN THE SOLUBILIZED PRODUCT |
|---|---|---|---|---|---|---|
| 2 | 20 | 500 | 1 | 1.2 | 3 | 80.3 |
| 3 | 20 | 500 | 2 | 2.4 | 3 | 87.4 |
| 4 | 20 | 500 | 3 | 3.6 | 3 | 91.9 |
| 5 | 20 | 500 | 4 | 4.7 | 3 | 92.9 |
| 6 | 20 | 500 | 5 | 5.9 | 3 | 93.2 |
| 7 | 20 | 500 | 7 | 8.3 | 3 | 95.1 |
| 8 | 20 | 500 | 3 | 3.6 | 24 | 100 |

TABLE 2

| | Dm (Pu) | $D_m$ (U) | Dm (FP) | Pu Kex $mol^{-6}_16$ | U Kex $mol^{-3}_13$ |
|---|---|---|---|---|---|
| 0.134 mol/l cis-syn-cis in $CHCl_3$ | 51 | 1.9 | 0.22 | 477 | 6.4 |
| 0.134 mol/l in $CHCl_3$ | 20 | 1.5 | 0.012 | 140 | 4.0 |
| 0.134 mol/l commercial DCH18C6 in $CHCl_3$ | 23 | 1.6 | 0.014 | 250 | 4.0 |

FIG. 1.
1. DCH18C6
2. SOLVENT
3. RECRYSTALLIZATION
4. FILTRATION
5. CRYSTALS OF ISOMER B (CIS-ANTI-CIS)
6. EVAPORATION
7. SOLVENT
8. PRECIPITATION
9. FILTRATION
10. ISOMER B
11. EVAPORATION
12. PURE ISOMER A (CIS-SYN-CIS)

What is claimed is:

1. Method for separating isomers of a crown ether compound having the formula

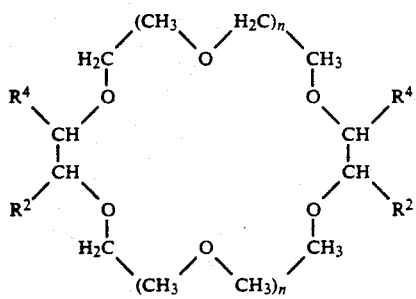

in which n=0 or is a whole number ranging from 1 to 3, $R_1$ and $R_2$, which are identical or different, represent an alkyl, alkoxyalkyl or poly(alkoxyalkyl) radical or $R_1$ and $R_2$ collectively form a cycloalkyl radical, wherein in includes the following successive stages:
   a) dissolving in an organic solvent a mixture of the isomers of said crown compound including the cis-anti-cis isomer and the cis-syn-cis isomer,
   b) adding uranyl nitrate to the solution obtained in stage a) in sufficient quantities so that virtually all the isomers, except the cis-syn-cis isomer, of the crown compound are precipitated in the form of complexes along with the uranyl nitrate,
   c) separating the formed precipitate, and
   d) recovering the remaining pure cis-syn-cis isomer from the solution.

2. Method according to claim 1, wherein the cis-anti-cis isomer is recovered from the precipitate separated in stage c).

3. Method according to claim 1 or 2, wherein it includes a preliminary stage consisting of separating one portion of the cis-anti-cis isomer present in the initial isomer mixture by dissolving the mixture in the organic solvent, by crystallizing the cis-anti-cis isomer present in this solution and by separating the crystallized cis-anti-cis isomer.

4. Method according to claim 1, wherein the organic solvent is an aliphatic saturated hydrocarbon or an aromatic hydrocarbon.

5. Method according to claim 3, wherein the organic solvent is an aliphatic saturated hydrocarbon or an aromatic hydrocarbon.

6. Method according to claim 5, wherein the organic solvent is heptane.

7. Method according to claim 1, wherein the crown compound responds to the formula:

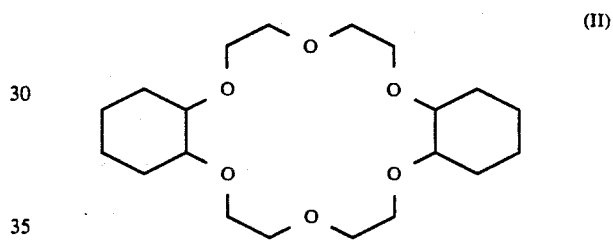 (II)

8. Method according to claim 7, wherein the quantity of the uranyl nitrate corresponds to 3.5 mols of uranyl nitrate $(NO_3)_2$ $UO_2/.6H_2O$ per mol of the cis-anti-cis isomer.

9. Method according to claim 3, wherein the crown compound responds to the formula:

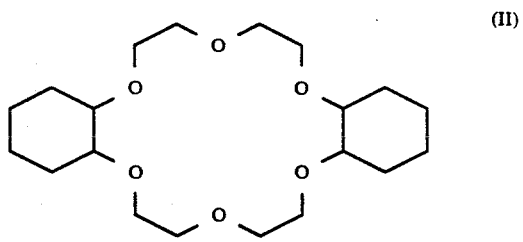 (II)

* * * * *

UNITED STATES PATENT AND TRADEMARK OFFICE
CERTIFICATE OF CORRECTION

PATENT NO. : 5,082,955
DATED : January 21, 1992
INVENTOR(S) : Marc Lemaire et al.

It is certified that error appears in the above-identified patent and that said Letters Patent is hereby corrected as shown below:

On the face of the patent, section [56] Other Publications, Column 2, the first reference, delete "Yaksin et al." and insert --Yakshin et al.--.

On the face of the patent, section [57], line 9 of the Abstract, delete "of".

Column 1, delete lines 20 - 30 and substitute the following:

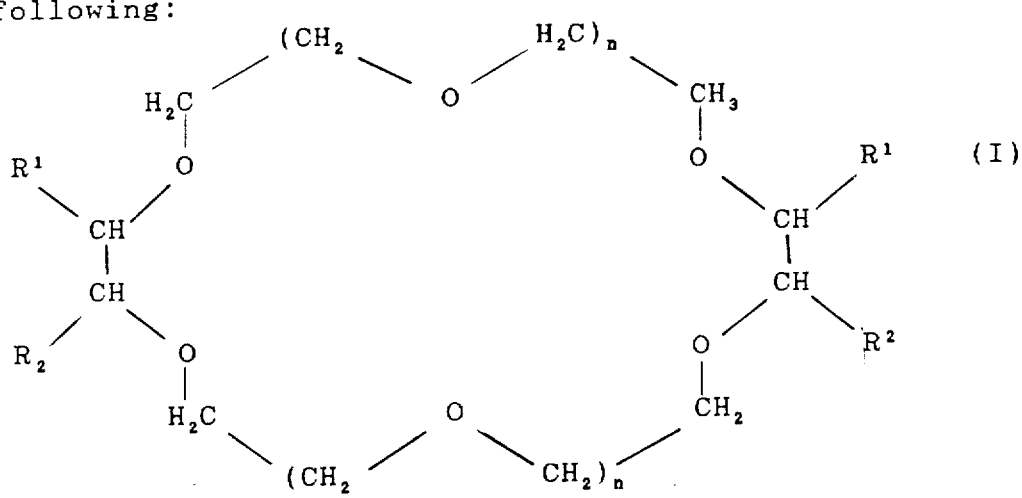

UNITED STATES PATENT AND TRADEMARK OFFICE
CERTIFICATE OF CORRECTION

PATENT NO. : 5,082,955

DATED : January 21, 1992

INVENTOR(S) : Marc Lemaire et al.

It is certified that error appears in the above-identified patent and that said Letters Patent is hereby corrected as shown below:

Column 3, delete lines 36 - 48 and substitute the following:

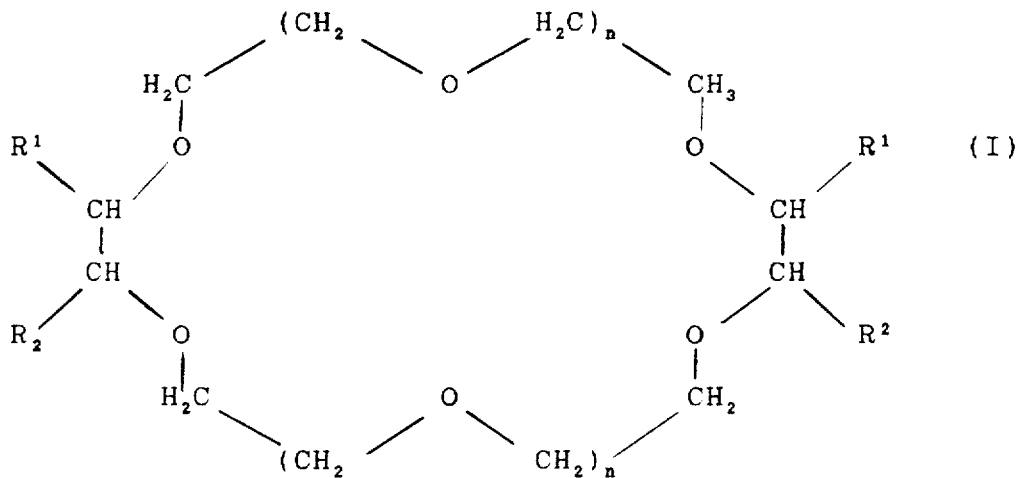

Column 8, line 19, delete "136" and insert --1360--.

UNITED STATES PATENT AND TRADEMARK OFFICE
CERTIFICATE OF CORRECTION

PATENT NO. : 5,082,955

DATED : January 21, 1992

INVENTOR(S) : Marc Lamaire et al.

It is certified that error appears in the above-identified patent and that said Letters Patent is hereby corrected as shown below:

Column 9, delete lines 31 - 43 and substitute the following:

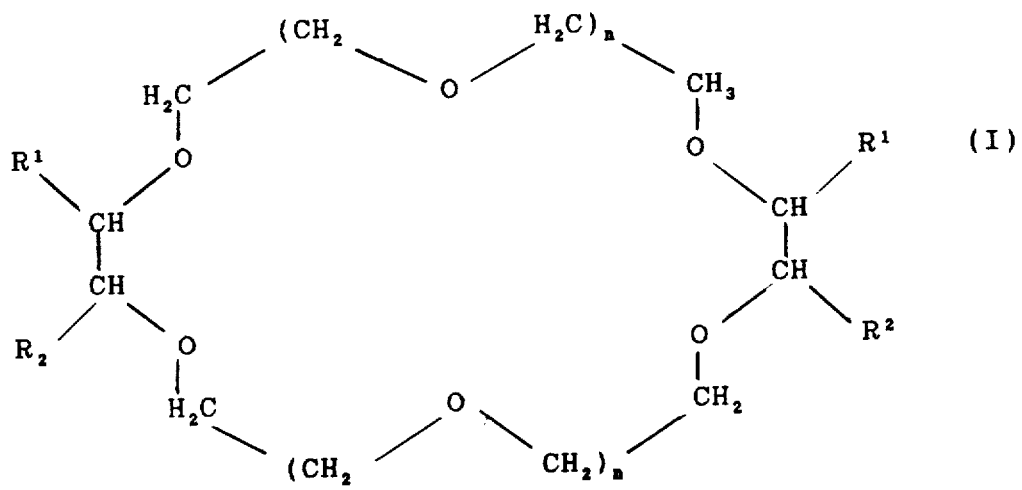

UNITED STATES PATENT AND TRADEMARK OFFICE
CERTIFICATE OF CORRECTION

PATENT NO. : 5,082,955

DATED : January 21, 1992

INVENTOR(S) : Marc Lemaire et al

It is certified that error appears in the above-identified patent and that said Letters Patent is hereby corrected as shown below:

Column 10, line 39 (claim 8, line 3), delete "$(NO_3)_2UO_2/.6H_2O$" and insert --$(NO_3)_2UO_2.6H_2O$--.

Signed and Sealed this

Twentieth Day of July, 1993

Attest:

MICHAEL K. KIRK

*Attesting Officer*   *Acting Commissioner of Patents and Trademarks*